(12) United States Patent
Myers

(10) Patent No.: US 6,704,210 B1
(45) Date of Patent: Mar. 9, 2004

(54) BIOPROTHESIS FILM STRIP FOR SURGICAL STAPLER AND METHOD OF ATTACHING THE SAME

(75) Inventor: David J. Myers, Garden Grove, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 08/993,922

(22) Filed: Dec. 18, 1997

Related U.S. Application Data

(60) Continuation of application No. 08/448,675, filed on May 24, 1995, now abandoned, which is a division of application No. 08/247,107, filed on May 20, 1994, now Pat. No. 5,478,006.

(51) Int. Cl.⁷ .............................................. H01R 9/09
(52) U.S. Cl. ...................... 361/773; 349/150; 361/776
(58) Field of Search ................. 174/250–261; 315/169.3, 169.4; 361/749, 772, 776, 773, 789; 349/149–152; 430/311; 439/67, 77

(56) References Cited

U.S. PATENT DOCUMENTS

| | | | |
|---|---|---|---|
| 4,766,426 A | * 8/1988 | Hatada et al. | 361/749 |
| 4,863,088 A | 9/1989 | Redmond et al. | 227/19 |
| 5,042,707 A | 8/1991 | Taheri | 606/213 |
| 5,203,864 A | 4/1993 | Phillips | 606/151 |
| 5,346,115 A | 9/1994 | Perouse et al. | 227/179 |
| 5,397,324 A | 3/1995 | Carroll et al. | 606/139 |
| 5,441,193 A | 8/1995 | Gravener | 227/176 |
| 5,470,007 A | 11/1995 | Plyley et al. | 227/175 |
| 5,489,058 A | 2/1996 | Plyley et al. | 227/176.1 |
| 5,542,594 A | 8/1996 | McKean et al. | 227/178.1 |
| 5,690,675 A | * 11/1997 | Sawyer et al. | 606/229 |
| 5,702,409 A | 12/1997 | Rayburn et al. | 606/151 |
| 5,769,892 A | * 6/1998 | Kingwell | 606/151 |
| 5,908,427 A | * 6/1999 | McKean et al. | 606/139 |
| 6,045,560 A | * 4/2000 | McKean et al. | 606/139 |
| 6,099,551 A | * 8/2000 | Gabbay | 606/219 |

FOREIGN PATENT DOCUMENTS

JP 61-210648 * 9/1986 .................. 438/611

OTHER PUBLICATIONS

Advertisement, "Breath Easy: Your Staple Line is Secure.", Seamguard Staple Line Reinforcement Material, W.L. Gore & Associates, The Annals of Thoracic Surgery, vol. 62, No. 5, Nov. 1996, ISSN: 0003–4975.

* cited by examiner

Primary Examiner—Gary Jackson
(74) Attorney, Agent, or Firm—Thomas G. Berry; Daniel W. Latham

(57) ABSTRACT

A bioprosthesis sealing film strip is attached to a surgical stapler by passing a jaw of the stapler through openings formed in the ends of the strip. Following stapling the strip is released by making a cut from the opening to the edge of the strip. Alternatively, one end of the strip may be releasably secured to pins formed on the jaw.

17 Claims, 5 Drawing Sheets

BIOPROTHESIS FILM STRIP FOR SURGICAL STAPLER AND METHOD OF ATTACHING THE SAME

This invention relates to surgical stapling guns, and more particularly to a bioprosthesis film strip to prevent air leaks at the staples in lung surgery, and to a method of attaching the strip to a stapling gun.

FIELD OF THE INVENTION

In various soft tissue surgery applications such as, for example, the resection of diseased lung tissue, surgeons use linear stapling guns to staple together layers of tissue on each side of a proposed cut along which the diseased tissue is to be severed from the healthy tissue. These stapling guns consist of a pair of elongated jaws which are clamped over, e.g., a lung from which a cancerous lobe is to be removed. One of the jaws carries a cartridge containing parallel rows of biocompatible staples positioned end-to-end, while the other carries parallel rows of anvils for those staples. Once the staples have been placed, a scalpel is drawn lengthwise between the staple rows to sever one stapled lung portion from the other.

Because of the nature of lung tissue, air leakage occurs at the points where the staples pierce the lung tissue, This leakage continues until the lung tissue heals around the staples, thus requiring lengthy hospitalization of the patient. To mitigate this problem, it has been proposed to drive the staples through a bioprosthetic film, which can act as a gasket or sealant to the lung tissue punctured by the staples. Suitable materials for this purpose are natural materials such as glutaraldehyde fixed bovine pericardium, or man-made materials such as collagen absorbable hemostat, vicryl (polygalacrin) mesh, or ePTEE (expanded polytetrafluoroethylene).

A problem arises when strips of these materials are to be applied to the jaws of the stapler in such a way that they can be conveniently released from the jaws after the stapling operation. For example, one prior method involves suturing a strip of bioprosthetic film to a strip of polyethylene backing to form a sleeve. One of these sleeves is then slipped over each jaw of the stapler, with the strip facing inward. After the stapling operation, the edges of the strips must be cut free of the hacking and Sutures, which are discarded. This method requires caution on the part of the surgeon to avoid leaving remnants of the backing or sutures in the patient.

Other methods of attachment have involved the use of glue or adhesive tape, but none of these are simple and satisfactory, A need therefore exists for a method of attaching a bioprosthetic film strip to a stapler jaw which is easy, reliable and allows the strip to be readily severed from the jaw.

SUMMARY OF THE INVENTION

The present invention fulfills the above-identified need by providing a flat bioprosthetic film strip with apertured ends. In one preferred embodiment of the invention, the perforated ends of the strip are simply turned our of the plane of the strip, and the jaw is slipped through them.

After the stapling, the strip can be released from the jaws in the preferred embodiment by cutting the strip adjacent the apertures, and the entire strip can be left in the patient.

In another preferred embodiment of the invention, the scrip can be secured to the jaw at the proximal end or at both ends with the aid of retaining pins from which ft can slip off when the jaws are opened following the stapling procedure.

BRIEF DESCRIPTION OF THE DRAWINGS

FIG. 1b is a section of the severed lobe edges along line 1b–1b of FIG. 1a;

FIG. 6 is a perspective view of a stapler using the strip of FIG. 5a;

DESCRIPTION OF THE PREFERRED EMBODIMENT

Figure 1A:
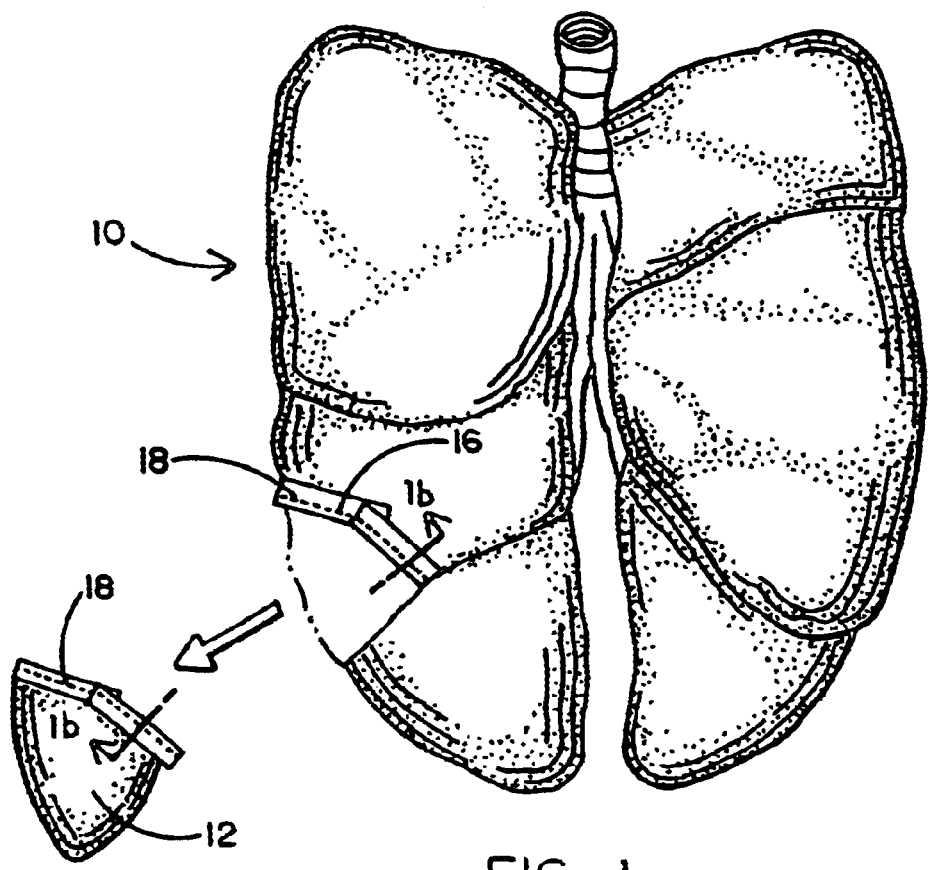
FIG. 1a is an elevational view of a lung showing a stapled and severed lobe.
Figure 1B:
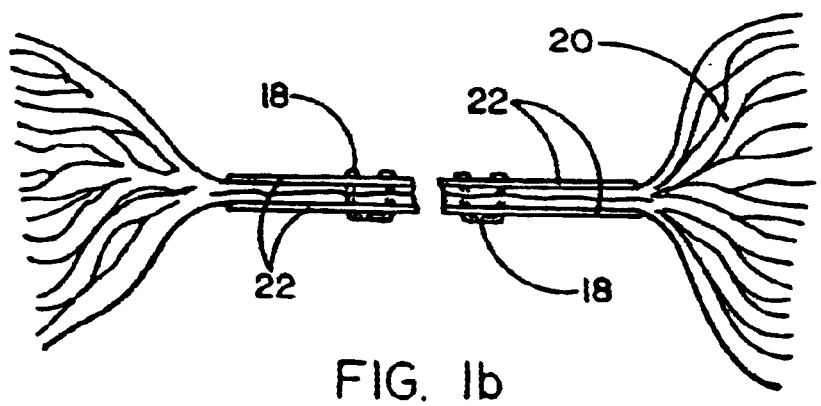
Figure 8:
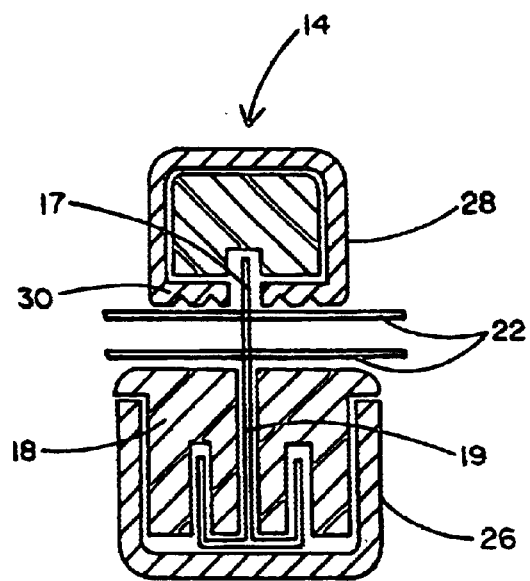
FIG. 8 is a section along line 8–8 of FIG. 7.

FIG. 1 illustrates an environment in which the present invention is useful. In that figure, it will be assumed that a lung 10 has a lobe 12 which is diseased and must be surgically removed. This is done by compressing the lung 10 between the jaws of a stapler 14 (FIG. 2) along a line 16 and stapling the lung with two parallel sets of rows of surgical staples 18 on each side of the line 16. The lung tissue is then cut along line 16 by a scalpel blade 17 traveling along a channel 19 (FIG. 8) between the two sets of rows. Typically, several overlapping stapled cuts are made at an angle to each other (see FIG. 1a).

In order to prevent excessive air leak from the lung tissue 20 (FIG. 1b) where it has been perforated by the staples 18, the staples 18 are conventionally driven through strips of a bioprosthetic sealing material 22 such as bovine pericardium, collagen absorbable hemostat, vicryl mesh or ePTFE. These materials effectively seal the punctured lung.

Figure 2:
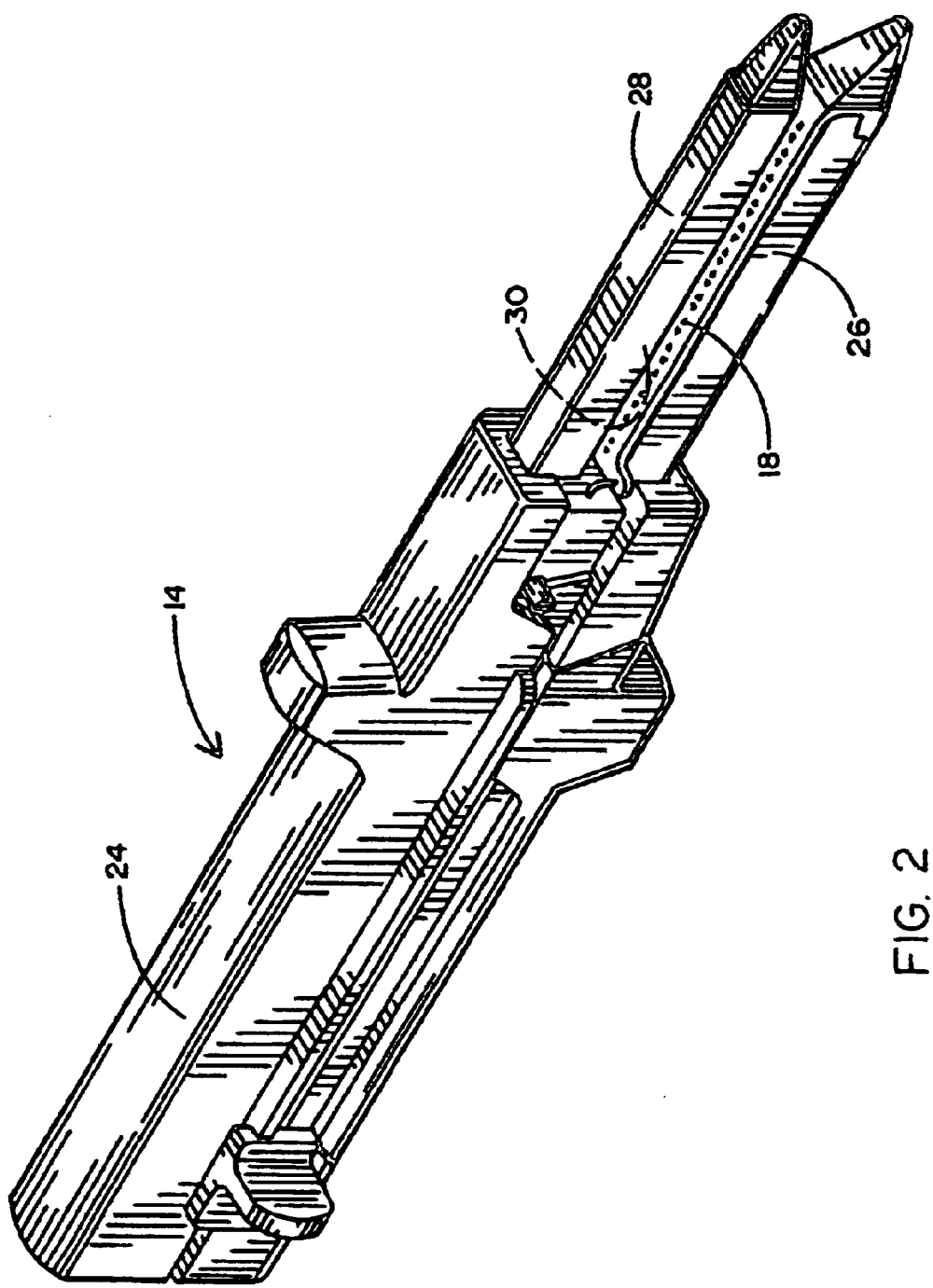
FIG. 2 is a perspective view of a typical stapling gun used for the stapling operation of FIG. 1.

FIG. 2 illustrates the stapler 14 which is used in the above-described procedure. The stapler 14 includes a handle 24 and a pair of jaws 26, 28. The jaws 26, 28 can be widely separated, like the jaws of pliers, prior to use, and then closed and compressed against each other in use. The jaw 26 carries a cartridge of staples 18, while the jaw 28 carries the anvil 30. In the use of the stapler 14, strips of the sealing material 22 (FIGS. 3 and 4) are placed over the staples 18 on jaw 26, and over the anvil 30 on the jaw 28. The strips 22 must be so mounted on the jaws 26, 28 that they are firmly held on the jaws 26, 28 but can be quickly and simply detached from the jaws 26, 28 in order to allow the jaws 26, 28 to be separated following the stapling.

Prior art solutions to this problem have included several different approaches. In one approach, a polymer backing was sutured to the strips 22 along their longitudinal edges, so that the strip and backing would form a sleeve which could be slipped over the jaws 26, 28. Following application of the staples, the sutures were cur, and the backing was removed, This was unsatisfactory because it required the cutting of a substantial number of sutures and the removal of the backing, all while holding the stapler in the closed position - a task sometimes exacerbated by misalignment of the sleeve with the jaw. Thus, this prior art approach presented a risk of accidentally leaving backing and suture fragments in the patient.

In another approach, biocompatible adhesives or adhesive tape were used to temporarily secure the strips 22 to the jaws 26, 28 but allow them to separate from the jaws when the jaws were opened. This was also unsatisfactory because it introduced additional foreign substances into the body, and because a repeatable acceptable compromise between sufficient adhesion for handling and sufficient releasability to avoid damaging the strips 22 after stapling was difficult to attain.

In accordance with a preferred embodiment of the invention, the above-described disadvantages are eliminated by providing strips 22 which extend longitudinally beyond the stapling area of the jaws 26, 28, and which have at least one hole, of a diameter approximating the diameter of the jaws, formed in the extended portion.

Figure 3:
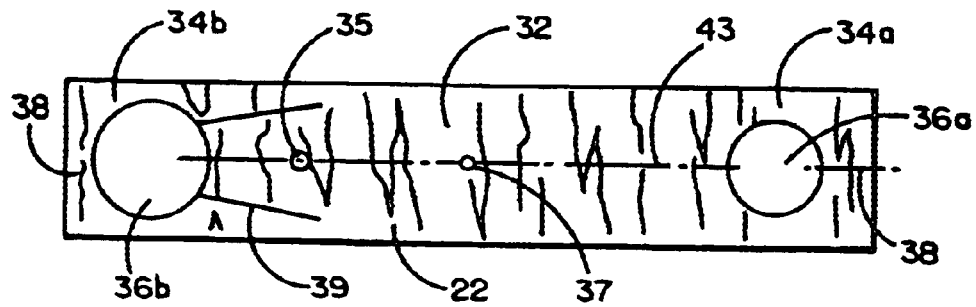
FIG. 3 is a plan view of a preferred embodiment of a bioprosthetic film strip used in the invention.

FIG. 3 shows that preferred embodiment of the invention. In that embodiment, the strip 22 has a central portion 32 whose length corresponds to the length of the stapling area of the jaw 26 or 28. At each end of the central portion 32, the strip 22 has an extension 34a or 34b. In the embodiment of FIG. 3, the extensions 34a has formed therein an opening 36a of appropriate size and shape (preferably rounded to provide an interference fit along the corners of the square jaws 26, 28) to allow passage of the jaw 26 or 28 therethrough. Preferably, the opening 36a in extension 34a is small enough to fit snugly over the distal end of jaw 26 or 28. In the extension 34b, an opening 36b is formed, and the strip 22 is cut along line 39. When the outer end of the extension 34b is lifted out of the plane of strip 22, the tongue 35 remains in the plane of the strip 22, The opening 36b in extension 34b is large enough w fit somewhat loosely, though with a small interference fit, over the proximal end of jaw 26 or 28.

The actual size of the openings 36a and 36b is dictated by several factors. On the one hand, the openings 36 must be large enough to allow the surgeon or stapler operator to slip or slide the strip 22 along the jaws 26, 28, yet small enough to hold the strip in position on the jaws 26, 28. On the other hand, the openings 36a and 36b must not be so small as to cause difficulty in slipping the strip 22 onto the jaws 26, 28, or to risk tearing the strip 22 during installation. As a practical matter, the openings 36a and 36b may be about 0.5–1.0 cm in diameter, the exact size depending upon the size and geometry of the jaws 26, 28. The strip 22 may, for example, be about 2 cm wide for a staple cartridge width of 1 cm.

Figure 7:
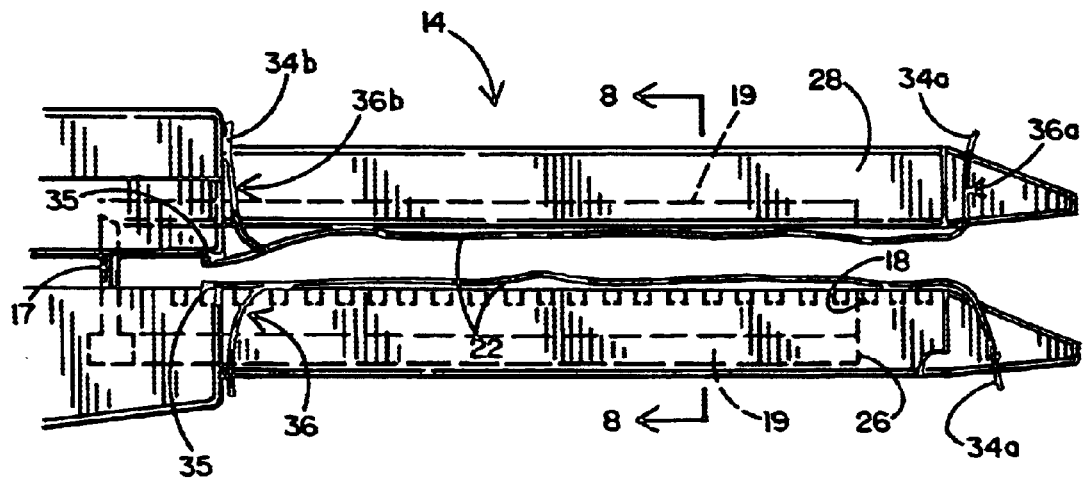
FIG. 7 is a side elevation of stapler jaws with the strip of FIG. 3 attached.

In a typical stapler (FIGS. 2 and 7), the staple cartridge 18 extends all the way to the proximal end of the jaw 26. Because the end portion 34b of the strip 22 lies at an angle to the jaw 26 or 28 (FIG. 7) when in stapling position, the end portion 34b is pre-cut along line 39 (FIG. 3). By bending the outer end of the extension 34b out of the plane of the strip 22, the opening 36b can be slipped over the end of the jaw, but the tongue 35 remains in the plane of strip 22 and covers the staple cartridge 18 or anvil 30 all the way to (he proximal end of the jaw 26 or 28.

Figure 4:
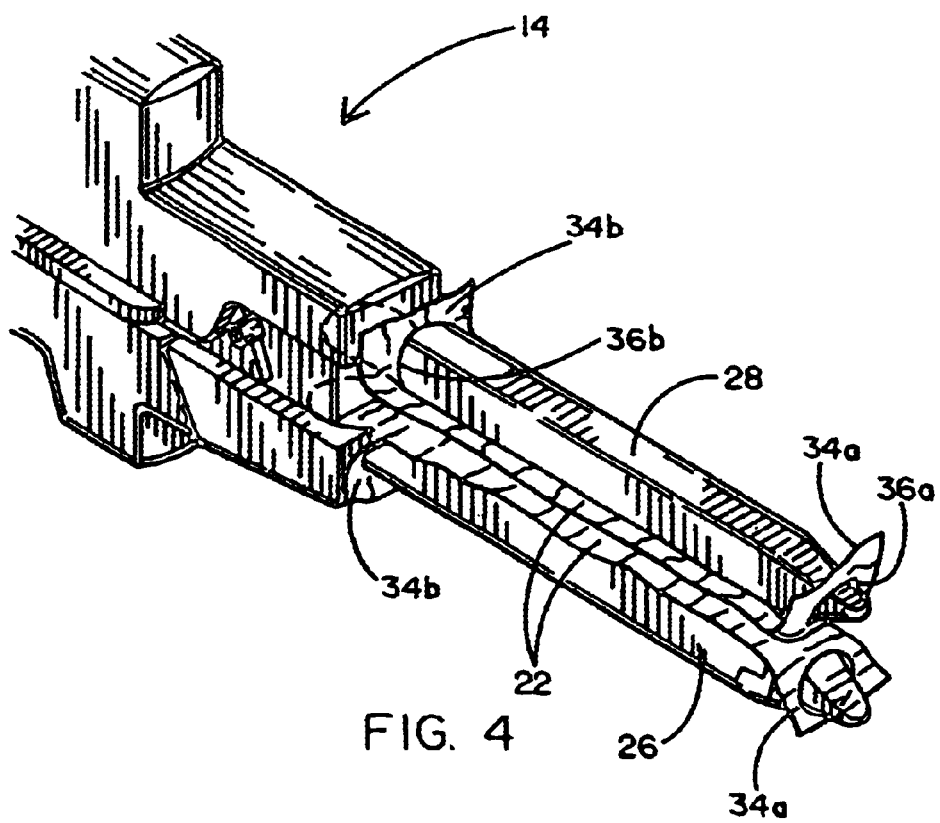
FIG. 4 is a perspective view of the jaws of the stapler of FIG. 2 with the strips of FIG. 3 attached.

In use, the extensions 34a and 34b are bent out of the plane of the strip 22, as shown in FIG. 4, and are simply slipped over the jaw 26 or 28. The resiliency of the flexible strip material (e.g. bovine pericardium) holds the strip 22 securely to the jaw 26 or 28. Following the stapling operation, the scalpel blade 17 is actuated to cut the lung tissue and the strips 22 along the dotted line 37. To release the strips 22 from the stapler, scalpel cuts are made by the operator at 38 in the protruding end portions 34a and 34b. Because in a typical stapler, the blade 17 does not travel all the way to the distal end of the stapling cartridge 18 (see FIG. 7), a further scalpel cut is needed at 43 after the jaws 26, 28 are removed to completely sever the healthy lung tissue and stapled strip halves from the diseased lung tissue and the stapled strip halves associated therewith.

Figure 5A:
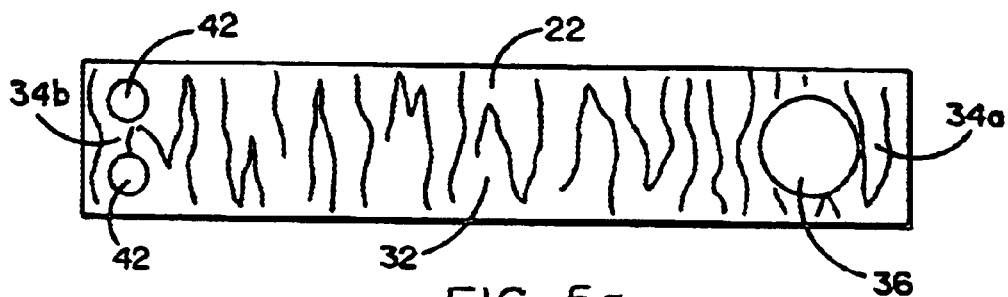
FIG. 5 is a plan view of a bioprosthetic film strip in an alternative embodiment of the invention.
Figure 6:
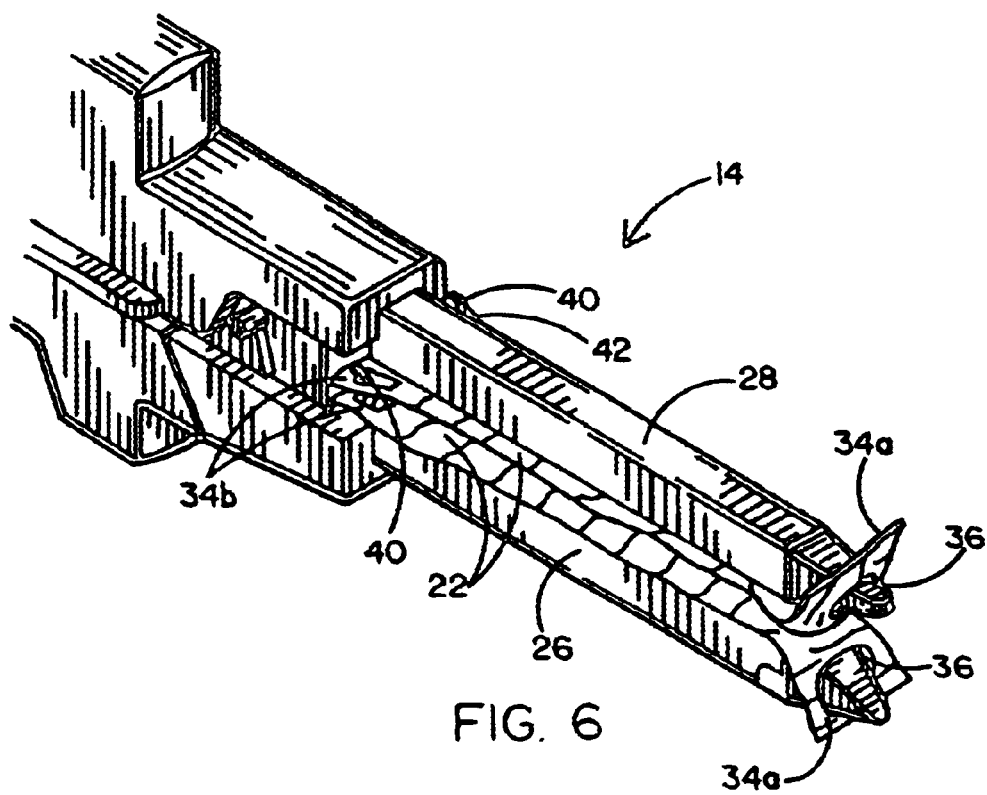

FIGS. 5a and 6 illustrate another preferred embodiment of the invention. In that embodiment, the stapler 14 has one or more pins 40 formed at the proximal end of at least one of the jaws 26, 28. The extension 34b has formed therein not a large opening 36b, but rather one or more small openings 42 that are preferably slightly smaller in diameter than the pins 40.

Figure 5B:
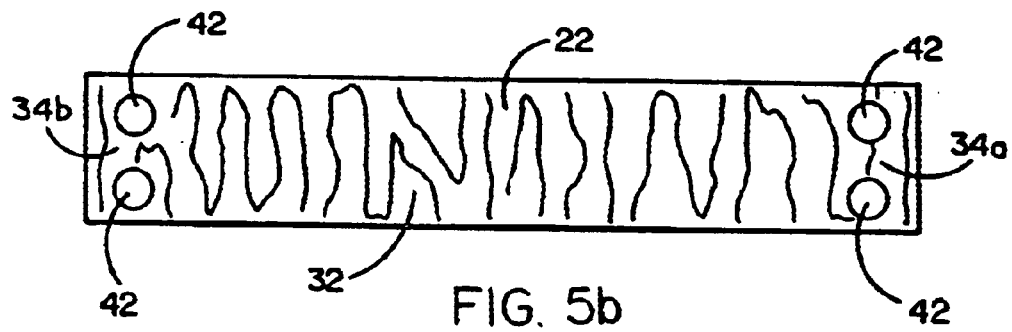

In the embodiment of FIGS. 5 and 6, the strips 22 are attached to the jaws 26, 28 by slipping opening 36 in extension 34a over the jaw 26 or 28, and then slipping the openings 42 of both strips 22 over the pins 40 on the jaw 26. The resilience of the strip material holds the strip 22 on the pins 40 prior to stapling but allows the scrip 22 to easily be pulled free of the pins 40 when the jaws 26, 28 are opened following stapling. It would also he possible to use pins 40 on both jaws 26, 28 and small openings 42 on both ends of the strip 22, in which case the opening 36 is unneeded (FIG. 5b). In that case, the strips 22 can be secured by simply hooking the openings 42 over the pins 40 and pushing the strips 22 against the stapling surfaces of the jaws 26, 28. With the diameter of the openings 42 being slightly smaller than the diameter of the pins 40, a firm but readily releasable engagement of the openings 42 with the pins 40 is achieved.

It is understood that the exemplary bioprosthesis film strips for surgical stapler described herein and shown in the drawings represent only presently preferred embodiments of the invention. Indeed, various modifications and additions may be made to such embodiments without departing from the spirit and scope of the invention. Thus other modifications and additions may be obvious to those skilled in the art and may be implemented to adapt the present invention for use in a variety of different applications.

What is claimed is:

1. A sealing strip for sealing staple punctures in soft tissue surgery, comprising:

a) a central elongated area adapted to receive surgical stapler.

b) an extension on each end of said central area, each of said extensions having formed therein a least one opening adapted to allow said strip to be temporarily secured to a jaw of a surgical stapler.

2. The sealing strip of claim 1, in which said opening in at least one of said extensions is large enough for said jaw to pass therethrough.

3. The sealing strip of claim 2, in which said opening in both said extensions is large enough for said jaw to pass therethrough.

4. The sealing strip of claim 1, in which said sealing strip is formed of animal pericardium.

5. The sealing strip of claim 1, in which said opening in one of said extensions is smaller than that in the other.

6. In combination, a surgical stapler having a pair of jaws carrying, respectively rows of staples and an anvil, and an elongated strip mounted on each of said jaws, said sealing strip comprising:

a) a central area of a length substantially equal to the length of said staple rows;

b) an extension on each end of said central area, each of said extensions having formed therein at least one opening arranged to allow said snip to be secured to said jaw.

7. The sealing strip of claim 6, in which said opening in at least one of said extensions is large enough for said jaw to pass therethrough.

8. The sealing strip of claim 6, in which said opening in both said extensions is large enough for said jaw to pass therethrough.

9. The sealing strip of claim 6, in which said sealing strip is formed of animal pericardium.

10. The combination of claim 6, in which at least one of said jaws has pins formed thereon, and one of said extensions has formed therein openings adapted to releasably engage at least one of said pins.

11. The combination of claim 10, in which the other of said extensions of said strip is secured to one of said jaws by passing said jaw through an opening formed in said extension.

12. The combination of claim 6, in which both of said extensions of said strip are secured to one of said jaws by passing said jaw through openings formed in said extensions.

13. The combination of claim 6, in which said jaws have upstanding pins formed thereon, and said openings in said ends of said central area are aligned with, and of slightly smaller diameter than, said pins.

14. A method of releasably securing a sealing strip to a jaw of a surgical stapler arranged to drive rows of staples through said sealing strip, comprising the steps of:
   a) providing an elongated planar strip of biocompatible sealing material having a central portion of substantially the same length as said staple rows, and extensions on each end of said central portion, said extensions each having at least one opening formed therein;
   b) bending at least one of said extensions out of the plane of said strip into a position substantially perpendicular to said jaw;
   c) passing said jaw through said opening;
   d) temporarily securing the other of said extensions to said jaw; and
   e) following a stapling operation, cutting said at least one of said extensions outwardly of said opening to disengage said strip from said jaw.

15. The method of claim 14, in which said other extension is secured to said jaw by passing said jaw through an opening therein.

16. The method of claim 14, in which said other extension is secured to said jaw by engaging at least one opening in said other extension with a pin formed on said jaw.

17. A sealing strip for sealing staple punctures in soft tissue surgery, comprising:
   a) a central flat elongated area adapted to receive surgical staples therethrough;
   b) a first extension formed on one end of said central area, said first extension having formed therein at least one opening adapted to allow said strip to be temporarily secured to a jaw of a surgical stapler; and
   c) a second extension formed on the other end of said central area, said extension having a cut therein of such extent and shape that, when a said portion of second extension is bent out of the plane of said strip, the bent portion defines an opening adapted to be slipped ova said jaw, while the reminder remains in said plane of said strip to form a flat extension of said central area.

* * * * *

UNITED STATES PATENT AND TRADEMARK OFFICE
CERTIFICATE OF CORRECTION

| | | |
|---|---|---|
| PATENT NO. | : 6,704,210 B1 | Page 1 of 2 |
| APPLICATION NO. | : 08/993922 | |
| DATED | : March 9, 2004 | |
| INVENTOR(S) | : David J. Myers | |

It is certified that error appears in the above-identified patent and that said Letters Patent is hereby corrected as shown below:

Column 4, line 43, that portion of the claim reading "stapler." should read --staples therethrough;--.

Column 4, line 47, that portion of the claim reading "stapler." should read --stapler; and c) wherein said sealing strip is a flat planar member.--.

Column 4, line 59, that portion of the claim reading "respectively rows" should read --respectively, rows--.

Column 4, line 67, that portion of the claim reading "said jaw." should read --at least one of said jaws.--.

Column 5, line 2, that portion of the claim reading "for said jaw" should read --for at least one of said jaws--.

Column 5, line 4, that portion of the claim reading "The scaling strip" should read --The sealing strip--.

Column 5, line 5, that portion of the claim reading "for said jaw" should read --for at least one of said jaws--.

Column 6, line 1, that portion of the claim reading "of :he" should read --of the--.

Column 6, line 16, that portion of the claim reading "sealing strip" should read --sealing planar strip--.

UNITED STATES PATENT AND TRADEMARK OFFICE
CERTIFICATE OF CORRECTION

PATENT NO. : 6,704,210 B1
APPLICATION NO. : 08/993922
DATED : March 9, 2004
INVENTOR(S) : David J. Myers It is certified that error appears in the above-identified patent and that said Letters Patent is hereby corrected as shown below:

Column 6, line 28, that portion of the claim reading "slipped ova" should read --slipped over--.

Signed and Sealed this

Eighteenth Day of September, 2007

JON W. DUDAS
*Director of the United States Patent and Trademark Office*